United States Patent [19]

Gala et al.

[11] Patent Number: 5,180,823
[45] Date of Patent: Jan. 19, 1993

[54] PROCESSES FOR PREPARING BICYCLIC COMPOUNDS

[75] Inventors: Dinesh Gala, East Brunswick; Martin Steinman, Livingston; Ashit Ganguly, Upper Montclair, all of N.J.

[73] Assignee: Schering Corporation, Kenilworth, N.J.

[21] Appl. No.: 773,184

[22] Filed: Oct. 8, 1991

Related U.S. Application Data

[62] Division of Ser. No. 435,634, Nov. 13, 1989, Pat. No. 5,079,360, which is a division of Ser. No. 178,176, Apr. 6, 1988, Pat. No. 4,897,487.

[51] Int. Cl.$^5$ ............... C07D 403/04; C07D 401/04; C07D 471/02; C07D 215/16
[52] U.S. Cl. ........................ 544/212; 544/233; 544/238; 544/350; 544/362; 546/123; 546/155; 546/275
[58] Field of Search ............. 544/212, 233, 238, 350, 544/362; 546/123, 155, 275

[56] References Cited

U.S. PATENT DOCUMENTS

| | | | |
|---|---|---|---|
| 4,452,800 | 1/1985 | Sherlock | 546/122 |
| 4,492,702 | 1/1985 | Sherlock | 546/122 |
| 4,628,055 | 2/1985 | Sherlock | 514/244 |
| 4,680,298 | 7/1987 | Blythin | 514/293 |
| 4,684,727 | 8/1987 | Blythin et al. | 544/127 |
| 4,794,116 | 12/1988 | Blythin et al. | 546/122 |

FOREIGN PATENT DOCUMENTS

| | | | |
|---|---|---|---|
| 0127135 | 12/1984 | European Pat. Off. | 514/244 |
| 116495 | 9/1977 | Japan | 514/244 |

OTHER PUBLICATIONS

CA 111:77987v Preparation of . . . agents. Blythin et al. p. 753, 1989.
CA 111:77988w Preparation of . . . heterocycles. Blythin et al. p. 753, 1989.
CA 115:159004u An efficient . . . SCH 37224. Nyce et al. p. 296, 1991.
Phosphorus Pentoxide in Organic Synthesis, III–A New Synthesis of Pyrido (2,3-d)-pyrimidin-4(3H)--ones, O. Andresen and E. Pedersen Liebigs Ann. Chem. 1982, pp. 1012–1015.
Lehman et al., Arch. Pharm., vol. 317, pp. 595–606 (1984).
Truitt et al., J.A.C.S., vol. 71, pp. 3479–3480 (1949).
Cram and Hammond, Org. Chemistry-McGraw-Hill, pp. 75–79 (1959).
Chem. Abstracts, 67535 vol. 72 (1970).

*Primary Examiner*—Mary C. Lee
*Assistant Examiner*—Joseph K. McKane
*Attorney, Agent, or Firm*—Joseph T. Majka; Edward H. Mazer; James R. Nelson

[57] ABSTRACT

The present invention relates to a process for preparing bicyclic compounds and intermediates thereof. The compounds are useful as anti-allergic, anti-inflammatory and/or cytoprotective agents.

5 Claims, No Drawings

PROCESSES FOR PREPARING BICYCLIC COMPOUNDS

This is a division of application Ser. No. 435,634 filed Nov. 13, 1989, U.S. Pat. No. 5,079,360, which is a division of application Ser. No. 178,176 filed Apr. 6, 1988, now U.S. Pat. No. 4,897,487.

FIELD OF THE INVENTION

The present invention relates to processes for preparing bicyclic compounds and intermediates thereof. Such compounds are useful as anti-inflammatory and/or cytoprotective agents.

BACKGROUND OF THE INVENTION

Processes for making certain bicyclic compounds and intermediates have been described in various publications, such an U.S. Pat. Nos. 4,684,727; 4,628,055; 4,680,298; 4,492,702; 4,452,800; in Japanese Patent Disclosure 11,649; in European Patent Application 0127135; and in the article "Phosphorous Pentoxide in Organic Synthesis, III"—A New Synthesis of Pyrido [2,3-d]-pyrimidin-4(3H)-ones, O. Andersen and E. Pederson Liebigs Ann. Chem. 1982, 1012–1015. It would be desirable to provides processes for preparing bicyclic compounds and their intermediates whose yields are as good as or better then methods previously taught. It would also be desirable to provide a process for preparing said bicyclic compounds and intermediates which requires even fewer steps than methods previously taught.

SUMMARY OF THE INVENTION

In one embodiment, the present invention is directed toward a process for preparing a bicyclic compound of a formula

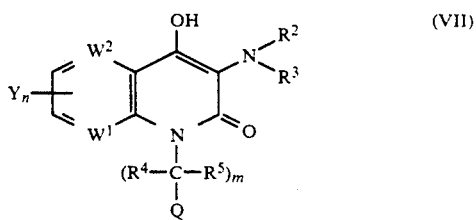

wherein $W^1$ and $W^2$ independently represent —CH= or —N=;

$R^2$, $R^3$, $R^4$ and $R^5$ independently represent H, alkyl having from 1 to 12 carbon atoms, alkenyl having from 3 to 8 carbon atoms, alkynyl having from 3 to 8 carbon atoms, alkoxyalkyl having from 1 to 6 carbon atoms in the alkoxy portion and from 2 to 6 atoms in the alkyl portion thereof, hydroxyalkyl having from 2 to 8 carbon atoms, cycloalkyl having from 3 to 8 carbon atoms, acyloxyalkyl having from 1 to 6 carbon atoms in the acyloxy portion and from 2 to 8 carbon atoms in the alkyl portion thereof, and —$R^6$—$CO^2R^0$ wherein $R^6$ represents an alkylene group having from 1 to 6 carbon atoms and $R^0$ represents hydrogen or an alkyl group having from 1 to 6 carbon atoms, with the provisos that the OH of the hydroxyalkyl group and the acyloxy of the acyloxyalkyl group are not joined to the same carbon atom as another heteroatom and that, when $R^2$ and/or $R^3$ are alkenyl or alkynyl, there is at least one carbon-carbon single bond between the nitrogen atom and the carbon-carbon double or triple bond and also with the proviso that $R^3$ does not represent hydrogen;

in addition, one of $R^2$ or $R^3$ can be an aryl group or an aromatic heterocyclic group, either of which can be substituted with one to three substituents Y as defined below;

in further addition, $R^2$ and $R^3$ can be joined together to represent a ring which can contain from 2 to 8 carbon atoms, said ring optionally containing a —O—, —S— and/or —NR4— heteroatomic group (wherein $R^4$ is as defined above) and/or optionally containing a carbon-carbon double bond, and said ring optionally being substituted with one to three additional substituents $R^7$ which substituents may be the same or different and are each independently selected from OH with the proviso that OH is not on a carbon already joined to a hetero atom, —O—acyl having from 1 to 6 carbon atoms, hydroxyalky having from 1 to 8 carbon atoms, alkoxyalkyl having from 1 to 6 carbon atoms in each alkyl portion thereof, alkyl having from 1 to 6 carbon atoms, alkenyl having from 3 to 8 carbon atoms, alkynyl having from 3 to 8 carbon atoms, —COOR$^{10}$ wherein $R^{10}$ is H, alkyl or aryl, or any two $R^7$ substituent groups may represent a hydrocarbon ring having from 4 to 8 total carbon atoms;

in still further addition, both $R^2$ and $R^3$ can be joined together to represent a polycyclic ring, which polycyclic ring can optionally be substituted by one to three substituents groups $R^7$ as defined above;

m is an integer of from 0 to 3;

n is an integer of from 0 to 2;

Q represents an aryl or an aromatic heterocyclic group which can optionally be substituted with 1 to 3 substituents Y as defined below;

each Y substituent is independently selected from the group consisting of hydroxy, alkyl having from 1 to 6 carbon atoms, halogen, $NO_2$, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, hydroxyalkyl having from 1 to 6 carbon atoms, —$S(O)_n$—$R^8$ (wherein $R^8$ represents alkyl having from 1 to 6 carbon atoms and n is as defined above), —$SO_2NH_2$, —CO—$R^9$ (wherein $R^9$ represents OH, —NH—$R^8$ or —O—$R^8$, where $R^8$ is as defined above), —O—B—$COR^9$ (wherein B represents an alkylene group having from 1 to 4 carbon atoms and $R^9$ is as defined above), —$NH_2$, —NHCHO, —NH—CO—$R^9$ (wherein $R^9$ is as defined above, with the proviso that it is not hydroxy), —NH—$COCF_3$, —NH—$SO_2R^8$ (wherein $R^8$ is as defined above), and —$NHSO_2CF_3$.

The process (i.e. Process A) comprises the step of contacting an amino acetamide compound of the formula

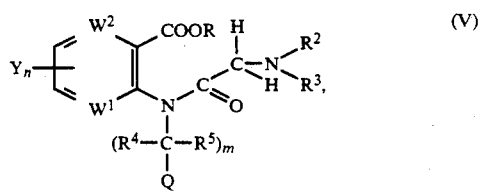

wherein

Y, $W^1$, $W^2$, $R^2$, $R^3R^4$, $R^5$, Q, m and n are as defined hereinbefore, and R is any of values for $R^4$ or $R^5$ with the proviso that R is not hydrogen, with a base effective to selectively remove a proton from the methyl group (i.e. —CH$_2$—) of said amino acetamide compound (V) in order to intramolecularly cyclize said compound to the bicyclic compound of formula (VII).

In preferred embodiments, as to the amino acetamide compounds of formula (V) preferably Y is hydrogen, $W^1$ is preferably nitrogen and $W^2$ is preferably CH, R is alkyl, more preferably methyl and m and 0, and $R^2$ and $R^3$ are joined together to represent a ring containing four carbon atoms, and Q is phenyl. Preferably the base is potassium t-butoxide. As to the bicyclic compound of formula (VII), preferably Y is hydrogen, $W^1$ is nitrogen, $W^2$ is CH, m is zero, Q is phenyl, and $R^2$ and $R^3$ are joined together to represent a ring of four carbon atoms. The process has the advantages of being able to prepare the compound of formula (VII) in high yield, good purity, with low by-product formation using relatively mild reaction conditions. The process also has the advantage of providing a reaction medium which allows a simplified means for recovery of the desired product.

Another embodiment of the present invention is directed to a second process (i.e. Process B) for also preparing bicyclic compounds of formula (VII). The process comprises the steps of contacting a secondary substituted amine of the formula

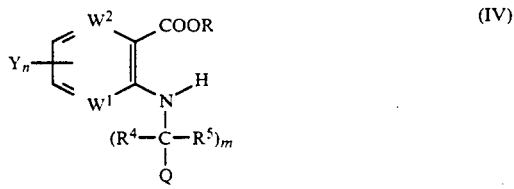

wherein

Y, $W^1$, $W^2$, $R^4$, $R^5$, Q, m and n are as defined hereinbefore;

with an amino-substituted acetic acid derivative of the formula:

$$R^1OOC-CH_2-NR^2R^3 \quad (VI)$$

wherein $R^2$ and $R^3$ are as defined hereinbefore; and $R^1$ represents the same values as for R;

with a base effective to cyclize said secondary substituted amine (IV) with said amino-substituted acetic acid derivative (VI) to give the desired bicyclic compound (VII).

As to the substituted secondary amine compound (IV) preferably Y is hydrogen, $W^1$ is nitrogen, $W^2$ is CH, R is as to the substituted secondary amine compound (IV), Q is phenyl and m is zero. As to the aminosubstituted acetic acid derivative, preferably $R^1$ is alkyl, preferably ethyl, $R^2$ and $R^3$ are joined together to represent a ring of four carbon atoms.

Also preferred is that the base is sodium hydride or potassium t-butoxide.

The present invention (i.e. Process B) has the advantages of being able to prepare the bicyclic compound (VII) in high yields and good purity with low-byproduct formation. Another advantage of the present invention is that it provides a process whose reaction mixture allows a simplified means of recovery of the desired bicyclic compound (VII).

In yet another embodiment, the present invention is directed toward a process (i.e. Process C) for preparing a substituted acetamide compound of the formula

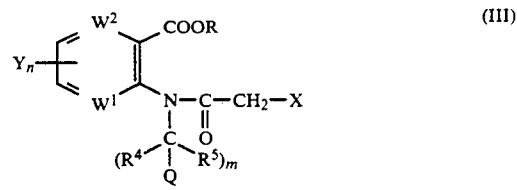

wherein Y, $W^1$, $W^2$, R, $R^4$, $R^5$, Q, m and n are as defined hereinbefore; and X is halogen.

The process comprises the step of contacting a secondary amine compound of the formula

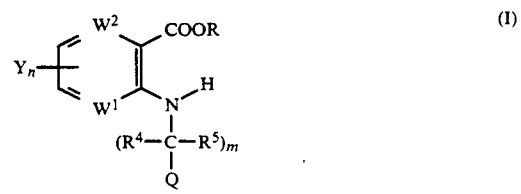

wherein

Y, $W^1$, $W^2$, R, $R^4$, $R^5$, Q, m and n are as defined hereinbefore; with a substituted acetic acid derivative of the formula $$X-CH_2COR^7 \quad (II)$$

wherein

X is as defined hereinbefore; and $R^7$ is a leaving group which is halogen, tosylate, mesylate or anhydride of the formula $$-OCOCH_2X^1$$

wherein $X^1$ is hydrogen or halogen; and said contacting is performed in the presence of a proton accepting compound. The substituted acetamide compound (III) is useful as an intermediate in preparing the bicyclic compound (VII).

With regard to the secondary amine compound (I), preferably Y is hydrogen, $W^1$ is nitrogen, $W^2$ is CH, R is alkyl, more preferably methyl, m is zero, and Q is phenyl.

With regard to the substituted acetic acid derivative of formula (II), preferably X is halogen and $R^7$ is halogen, more preferably chloro. Where the leaving group is an anhydride preferably Xl is halogen, more preferably chloro. Preferably the proton accepting compound is an epoxide, most preferably propylene oxide. The process of the present invention (i.e. Process C) has the advantage of providing a process useful for preparing a substituted acetamide compound (III) useful for subsequently preparing the bicyclic compound (VII). The present process also has the advantage of preparing substituted acetamide compounds (III) in high yields, good purity, with low by-product formation using relatively mild reaction conditions.

DETAILED DESCRIPTION OF THE INVENTION

Process A

-continued

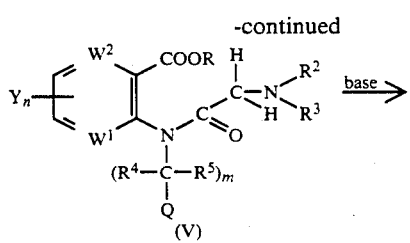

-continued

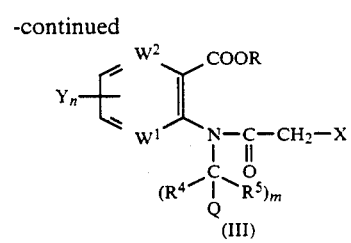

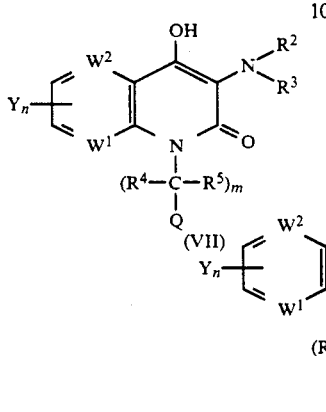

It is understood and intended that the bicyclic compounds (VII) prepared by the processes of the present invention can exist in a zwitterionic form, such as illustrated below.

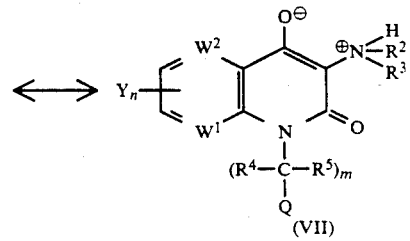

When utilized herein the terms listed hereinbelow, unless otherwise indicated, are defined as follows:

halogen or halo—fluoro, chloro, bromo and iodo;
alkyl and alkoxy—comprise straight and branched carbon chains and, unless otherwise specified, contain from 1 to 6 carbon atoms;
alkenyloxy—comprise straight and branched carbon chains and, unless otherwise specified, contain from 3 to 8 carbon atoms and comprising a carbon to carbon double bond;
alkynyloxy—comprise straight and branched carbon chains and, unless otherwise specified, carbon from 3 to 8 carbon atoms and comprising a carbon to carbon triple bond;
aryl—a carbocyclic group containing at least one benzene ring, with the aryl groups preferably containing from 6 to 15 carbon atoms, more preferably being phenyl or Y-substituted phenyl, e.g., phenyl, naphthyl, indenyl, indanyl, 4-chlorophenyl, 4-fluorophenyl, etc.;
aromatic heterocyclic—cyclic groups having at least one O, S and/or N heterogroup interrupting the ring structure and having a sufficient number of unsaturated carbon to carbon bonds, nitrogen to carbon bonds, etc., to provide aromatic character, with the aromatic heterocyclic groups preferably containing from 4 to 14 carbon atoms, e.g., pyridyl, furyl, thienyl, thiazolyl, imidazolyl, pyrimidinyl, pyrazinyl, pyridazinyl, 1,2,4-triazinyl, benzofuranyl, indolyl, pyrazolyl, oxazolyl, etc. Many times such heterocyclic groups can be bonded via various positions on the ring and all such variations are contemplated, e.g. 2- or 3-furanyl, 2-, 3- or 4-pyridyl, etc.

Process B

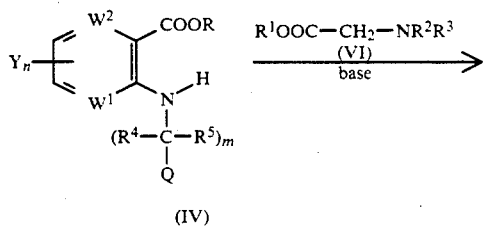

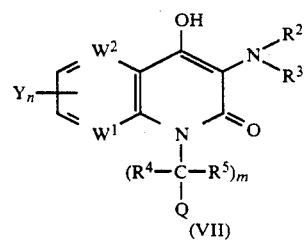

Process C

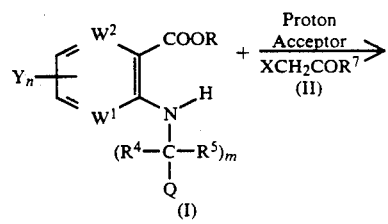

The compounds of the invention are comprised of a $-(CR^4R^5)_m-$ substituent wherein each $R^4$ group and each $R^5$ group may vary independently. Thus, for example, when m equals 2 the following patterns of substitution (wherein hydrogen and $CH_3$ are used to represent any substituent, $R^4$ or $R^5$) are contemplated:
$-C(CH_3)_2CH(CH_2-$, $-CH_2C(CH_3)_2-$, $-CH_2CH(CH_3)-$, $-CH(CH_3)CH_2-$, $-(C(CH_3)H)_2-$ and the like. In addition when m equals 3, substituents such as $-C(CH_3)_2CH(C_2H_5)-CH_2-$, $-CH(CH-$ 3)—CH₂CH(C₂H₅)—, and CH₂—CH(i—C₃H₇)CH(C₂H₅)— are also contemplated.

The R² and R³ groups on the amino nitrogen in the compounds of the invention can be the same or different. In some instances as noted above, two of such groups or three of such groups may together represent a heterocyclic ring system with the nitrogen of the amino group being part of such ring, e.g., a monocyclic or bicyclic ring. Examples of suitable —NR²R³ groups include the protonated secondary amino groups such as —NH(CH₃), —NH(—CH₂—CH=CH₂), —NH(phenyl), —NH(—CH₂—CH=CH₂), —NH(phenyl), —NH(4-pyridyl), etc.; tertiary amino groups such as —N(CH₃)₂, —N(CH₂CO₂H)C(CH₂OH)₃, etc.;

As noted above, the compounds of the invention may include one to three Y substituents on the bicyclic ring system. Also, the Q group may include one or two Y substituents. In cases where there is more than one such Y substituent, they may be the same or different. Thus, are contemplated within the scope of the invention. Examples of suitable Y substituents include OH, methyl, chloro, bromo, methoxy, cyclohexyl, allyloxy, 2-propynyloxy, hydroxyethyl, methylthio, methylsulfonyl, carboxy, acetoxy, N-methylaminocarbonyl, acetoxymethoxy, acetamido, methylsulfonamido and the like.

Turning to the processes of the present invention, in process A the bicyclic compounds of formula (VII) are prepared by contacting an amino acetamide compound of formula (V) with a base in amounts and under conditions effective to selectively remove a proton from the methyl group of said amino acetamide compound (V) in order to intramolecularly cyclize said compound (V). The amino acetamide compound of formula (V) can be contacted with the base at temperatures ranging from about −100° C. to about 100° C., preferably from about −70° C. to about 40° C., depending upon the base employed. The reactants can be contacted at ambient pressures although pressures less than or greater than ambient can be employed. The reactants can be stirred or not stirred during the contacting, although stirring is preferred. The reactants are contacted for a time effective to complete the reaction to the desired extent, for a period ranging from about 5 minutes to about 24 hours or more. The contacting can be conducted neat although generally compatible solvents can be employed. Such solvents include but are not limited to the chlorinated, hydrocarbons such as carbon tetrachloride (CCl₄), methylene chloride (CH₂Cl₂), and dichloroethane; to aliphatics such as C-1 to C-20 alkanes, cyclic or acyclic; aromatics such as benzene, toluene, xylene, alkylbenzenes and the like; to ethers such as diethyl ether and tetrahydrofuran (THF) and tertiary butylmethyl ether; and to solvents such as dimethylformamide (DMF), dimethylsulfoxide (DMSO), or mixtures thereof.

The base employed in Process A is any substance which will remove a proton from the methyl (—CH2—) group of the moiety

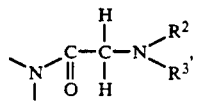

in order to intramolecularly cyclize the amino acetamide compound of formula (V).

Bases which can be employed in process A are generally non-aqueous bases such as organo-alkali metals such as primary, secondary and tertiary butyl lithiums, such as lithium diisopropyl amide, lithium hexamethylsilazenes, sodium hexamethylsilazenes and potassium hexamethylsilazenes; potassium t-butoxide or sodium methoxide; bases of alkali and alkaline earth metals including carbonates such as sodium, potassium and cesium carbonates; hydroxides such as sodium and potassium hydroxides; hydrides such as sodium or potassium hydrides; preferably the base is sodium hydride, sodium methoxide, most preferably potassium t-butoxide. Other bases which may be suitably employed are disclosed in "Modern Synthetic Reactions" by H. House, W.A. Benjamin, Inc., Menlo Park, Calif., 1972, 856 pages. The amino acetamide compounds of formula (V) can be contacted with the base in an amount effective to cyclize compound (V). The amount of base is employed in ratios ranging from about 1,000 to 2:1 mole; preferably from about 20 to 2:1, most preferably from about 8 to 2:1 (moles of base:mole amino acetamide (V)). Where employed, the solvents can range from about 1% to about 500% by weight of the amino acetamide compound (V).

After the reaction is completed, the desired bicyclic compound of formula (VII) is recovered by conventional separatory and recovery methods such as chromatography, distillation, crystallization and the like.

In process B for preparing the bicyclic compound of formula (VII), a secondary substituted amine of formula (IV) is contacted with an amino-substituted acetic acid derivative of formula (VI) in amounts and under conditions effective to yield the desired bicyclic compound of formula (VII). The bases and solvents employed in process B are essentially the same as those in process A, described hereinbefore. The secondary substituted amine of formula (IV) is contacted with the amino-substituted acetic acid derivative of formula (V) at temperatures ranging from about −40° C. to about 200° C., preferably from about 25° C. to about 180° C. The contacting is performed at ambient pressures although pressures is greater or less than ambient can be employed. The contacting of the reactants can be carried out from about 5 minutes to about 72 hours or more until the reaction is substantially completed, preferably from about 1 hour to about 48 hours. Also preferred is that the reactants are stirred during the contacting procedures. The amino-substituted acetic acid derivatives of formula (VI) can be contacted with the secondary substituted amines of formula (IV) in ratios ranging from about 100 to 1:1 mole; preferably from about 10 to 1:1, most preferably from about 6 to 1:1 (moles amino-substituted acetic acid derivative (VI):mole secondary substituted amine (IV)).

The base is employed in amounts ranging from about 1,000 to 3:1 mole, preferably from about 330 to 3:1, most preferably from about 15 to 3:1, (moles base:mole secondary substituted amine (IV)).

The reactants can be contacted neat, although preferably a solvent is employed. A solvent can be employed in amounts ranging from about 1 to 5,000% by weight of the secondary substituted amine (IV), preferably from about 2% to about 1,000% by weight, more preferably from about 2 to 50 percent.

After the reaction is completed, the desired bicyclic compound of formula (VII) is recovered by conventional separatory and recovery methods such as described hereinbefore.

In yet another embodiment of the present invention, i.e. process C, the substituted acetamide compound of formula (III) is prepared by contacting a secondary amine compound of formula (I) with a substituted acetic acid derivative of formula (II) in the presence of a proton acceptor in amounts and under conditions effective to give the substituted acetamide compound (III).

The substituted acetic acid derivative (II) is employed in amounts ranging from about 100 to 1:1 mole, preferably from about 25 to 1:1, most preferably from about 5 to 1:1 mole (moles substituted acetic acid derivative (II): mole secondary amine compound of formula (I)).

The term "proton acceptor" is defined as a compound which accepts either a proton from an acid, or free protons in the reaction mixture, but generally will not accept a proton from the methyl group of the formula

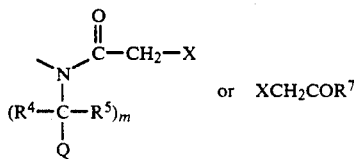

or $XCH_2COR^7$ wherein —$CH_2$— is the methyl group. The proton acceptor should be compatible with the reactants and can be a base such as ammonia ($NH_3$) or an organic base including amines such as methylamine, β-naphthylamine, aniline, n-butyl amine, sec-butylamine, tert-butylamine, p-toluidine, 2,3-dimethylbenzenamine, 2-phenylethanamine, benzylamine, cyclohexylamine, ethylamine, ethylenediamine, o-toluidine, m-toluidine, p-toluidine, urea; a secondary amine or a compound containing at least one secondary amine such as dimethylamine, diphenyl amine, N-methylpropylamine, diethylamine, diisopropyl amine, N-methylaniline, piperazine, piperidine, pyrrolidine; a tertiary amine such as trimethylamine, dimethylaniline, N,N-dimethyl-n-propylamine, N-methylpiperidine, N,N-diethylbutylamine, triethylamine; heterocyclic nitrogen containing compounds such as isoquinoline, morpholine, purine, pyridine, pyrazine, pyrimidine, quinoline or polyvinyl pyridine; or to inorganic bases such as those of alkali or alkaline earth metals discussed hereinbefore. The proton acceptor can also be an epoxide of the formula:

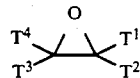

wherein $T^1$, $T^2$, $T^3$ and $T^4$ independently represent hydrogen, alkyl, alkenyl, alkynyl, alkoxyalkyl, hydroxyalkyl, cycloalkyl, as defined hereinbefore, and phenyl, halophenyl, alkyl phenyl having 1 to 6 carbons in the alkyl portion, alkoxyphenyl having 1 to 6 carbons in the alkoxy portion, benzyl, halo benzyl, alkyl benzyl having 1 to 6 carbons in the alkyl portion, alkoxy benzyl having 1 to 6 carbon atoms in the alkoxy portion, halo alkyl and cycloalkalkyl having 1 to 6 carbon atoms in the alkyl portion. Representative epoxides suitable as proton acceptors include but are not limited to ethylene oxide, propylene oxide, ethyl glycidate, epichlorohydrin, styrene oxide or mixtures thereof; and also to polymer bound and/or supported epoxides. Preferably, the epoxide is propylene oxide. Alternatively, the epoxide can be prepared in-situ in the reaction mixture. The proton acceptor can also include mixtures of the base and epoxide whose ratios can range from about 0.0001 to 10,000 parts by weight base to 1 part by weight epoxide.

The proton acceptor or accepting compound is used in amounts effective to effectively scavange the requisite protons. Such amounts can range from about 10,000 to 1:1 mole, preferably from about 100 to 1 mole:1, most preferably from about 20 to 1:1 mole (moles proton acceptor:mole secondary amine compound of formula (I)).

Process C can be conducted neat, although a solvent is preferred. Where a solvent is employed the contacting is conducted in the presence of a solvent whose amounts can range from an amount sufficient to at least partially solubilize one or both of the reactants and/or the desired product to an excess of either starting reactant. Generally the amount of solvent can range from about 1 to 5,000 percent or more by weight of the individual reactant, preferably from about 2 to 1,200 percent by weight. The contacting of the reactants is conducted for a time effective to substantially complete the reaction, preferably from about 5 minutes to about 24 hours or more, preferably from about 15 minutes to about 4 hours. Generally the reactants are stirred during the contacting.

Optionally, the process can be conducted in the presence of a catalyst such as N,N-dimethylaniline, 4-dimethylaminopyridine or phase-transfer catalysts. The term "phase transfer catalyst" is intended to mean a material which catalyzes a reaction by the transfer of one phase to another. Phase transfer catalysts suitable for carrying out the process of the present invention include the quaternary ammonium and phosphonium salts, ethers and tertiary amines, such as tributyl amine, such as those described in U.S. Pat. No. 3,969,360.

Where a catalyst is employed, a catalytic amount is used ranging from about 0.0001 to about 0.5 parts by weight of reactant, preferably from about 0.001 to about 0.1 parts by weight.

The reactants are contacted in Process C at a temperature effective to yield the derived product, generally at temperatures ranging from about −40° C. to about 200° C., preferably from about 0 to about 80° C., depending upon the boiling point of the epoxide, solvent or starting materials. The contacting is performed at ambient pressures, although pressures greater than or less than ambient can be employed.

The following examples illustrate the present invention in a manner of which it can be practiced but, as such, should not be construed as limitations upon the overall scope of the same.

EXAMPLE 1

PREPARATION OF
4-HYDROXY-1-PHENYL-3-(1-PYRROLIDINYL)-
1,8-NAPHTHYRIDIN-2-(1H)-ONE

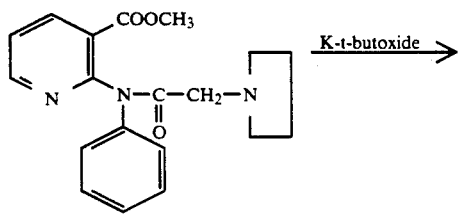

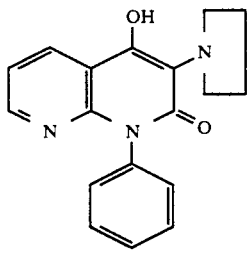

To a suspension of 1.4 g (4.1 millimoles (mM) of 3-pyridinecarboxylic acid-2(((1-pyrrolidinyl)acetyl)phenylamino)methyl ester in t-butylmethylether at 0° C.-5° C., 1.03 g (9.2 mM) potassium-t-butoxide is added. The reaction mixture is stirred for an additional 0.5 hour at 0° C.-5° C. and allowed to warm up to room temperature. Next 0.75 mL glacial acetic acid is added very slowly. The resultant solid is filtered, washed with t-butylmethylether, methylene chloride, acetone, water and acetone. The product is air dried to give 0.94 g (73% yield) of title compound, a white solid.

EXAMPLE 2

PREPARATION OF 4-HYDROXY-1-PHENYL-3-(1-PYRROLIDINYL)-1,8-NAPHTHYRIDIN-2-(1H)-ONE

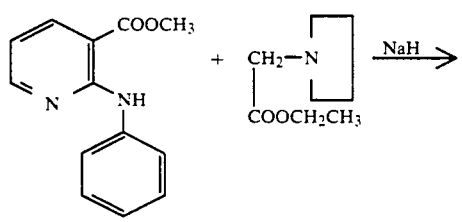

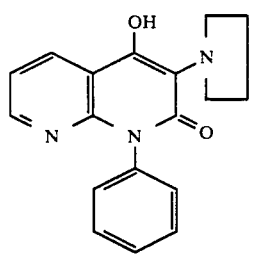

To a solution of 1.5 g (6.5 mM) 2-anilinonicotinic acid, methylester, in dry xylenes at room temperature is added 0.69 g (14.54M) of sodium hydride (NaH) (50 percent (%) oil emulsion) followed by addition of a small amount of N,N-dimethylformamide (DMF). The reaction mixture is heated to a temperature ranging between 85-95 degrees Centigrade (° C) and 1.05 milliliters (mL) (6.5 mM) of ethyl-1-pyrrolidineacetate in xylene is slowly added over a period of 10 minutes. The reaction mixture is heated for 1 to 3 hours prior to the addition of aliquots of 0.32 g NaH followed by 1.05 mL of ethyl-1-pyrrolidineacetate as described above (total 3 aliquots). Following addition of the aliquots, the reaction mixture is cooled to 0° C., quenched with a slow addition of glacial acetic acid, and then water is added. The product is filtered and washed with water, acetone, methylene chloride, and acetone. The solid then obtained is dried in vacuo to give 1.20 g (60% yield) of title compound, a white solid.

EXAMPLE 3

PREPARATION OF 3-PYRIDINE CARBOXYLIC ACID, 2-((CHLOROACETYL)PHENYLAMINO), METHYLESTER

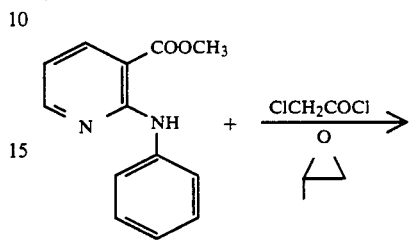

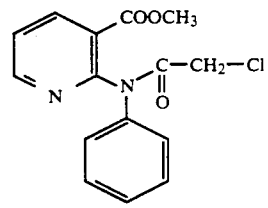

To a stirred solution of 26.3 g 2-anilinonicotinic acid methylester (11.5 mM) in t-butylmethylether at 50° C. (oil bath) under nitrogen atmosphere, 20.2 mL chloroacetylchloride (25.39 mM) followed by 32.4 mL propylene oxide (46 mM) is added. The reaction mixture is stirred at 50° C. for 2 additional hours, cooled to room temperature, diluted with t-butylmethyl ether and washed with water containing NaHCO$_3$. The layers are separated, the aqueous layer is extracted with t-butylmethylether, the combined organic layers are dried over anhydrous Na$_2$SO$_4$ and concentrated in vacuo to obtain a gummy solid which is recrystallized from t-butylmethyl ether to give 30.5 g (87% yield) of title compound, an off-white solid.

IR (CHCl$_3$) 1700,1740 cm$^{-1}$,
NMR (CDCl$_3$ δ4.1 (chloromethyl).

EXAMPLE 4

PREPARATION OF 1-(1,2-DIHYDRO-4-HYDROXY-1-PHENYL-2-OXO-1,8-NAPHTHYRINDIN-3-YL-)-PYRROLIDINIUM

HYDROXIDE, INNER SALT

Step A: To a stirred solution of 25.45 g (0.11M) of methyl-2-phenylamino-nicotinate in 160 mL of t-butyl methyl ether (tBuOMe) (dried over 3Å sieves) heated to 50° (under N$_2$) 19.5 mL (2.2×0.11M) of chloroacetylchloride followed by 31 mL (4×0.11M) of propylene oxide was added. The reaction mixture was heated at 50° C. for 1.5 hours and then 300 mL tBuOMe was added. This solution (cooled to room temperature) was washed with 200 mL H$_2$O containing 9.37 g (0.11M) of NaHCO$_3$ followed by 30 mL of saturated aqueous NaCl solution. At this stage the product that crystallized out was dissolved in 100 mL CH$_2$Cl$_2$ and this CH$_2$Cl$_2$ was mixed with tBuOMe solution. The solution, as is, was used for the next reaction.

Step B: To the above solution at room temperature under N$_2$, 37.2 mL (4×0.11M) of pyrrolidine was added and this solution was gently refluxed overnight. 9.3 mL (0.11M) of pyrrolidine was added, and the reaction was refluxed for an additional two hours. This mixture was diluted with 600 mL tBuOMe and washed with 300 mL H2O and the aqueous layers were back extracted with 200 mL tBuOMe. The combined organic (tBuOMe) layer was washed with 150 mL saturated aqueous NaCl soln., dried over anhydrous Na2SO4, and then concentrated in vacuum (oil pump vacuum) to 64.6 g of a crude brown semisolid, which was the methyl ester of 2-[[1-pyrrolidinyl acetyl]phenylamino]-3-pyridine carboxylic acid.

Step C: The solid from step B above was suspended in 600 mL of cold (0° C.) tBuOMe (dried over 3Å sieves) under N2. To this cold stirred mixture, 27.5 g (2.2×0.11M) potassium t-butoxide was added, the reaction mixture was stirred for 1 hour, and then it was quenched with 15 mL (2.4×0.11M) of glacial acetic acid.

The stirred reaction mixture was allowed to attain room temperature and then 350 mL H2O was added to it. The resultant solid was filtered, washed with tBuOMe, H2O, a small amount of CH2Cl2, acetone, and then air dried to obtain 27.09 g of the white product 1-(1,2-dihydro -4-hydroxy-1-phenyl-2-oxo-1,8-naphthyridin-3-yl)-pyrrolidinium hydroxide, inner salt. The crude product was crystallized from 300 mL CH3OH+16 mL conc. H2SO4 at 50° C.+3 g carbon; filtered, diluted with 575 mL H2O, cooled to 0° C. and filtered; and draft oven dried at 60° C. for about 18 hours to give 22.2 g (82%) of crystallized white product.

PREPARATION OF STARTING MATERIALS

The starting materials employed in processes A, B and C are known or can be prepared from known procedures. See, for example, U.S. Pat. Nos. 4,684,727; 4,452,800, 4,492,702 and 4,680,298 whose preparative teachings are incorporated herein by reference.

The present example, illustrates one method of which starting materials of the present invention may be prepared, but as such, should not be contrued as limitations upon the overall scope of the same.

EXAMPLE 5

PREPARATION OF 3-PYRIDINE CARBOXYLIC ACID, 2(((1-PYRROLIDINYL)ACETYL)-PHENYLAMINO)METHYL ESTER

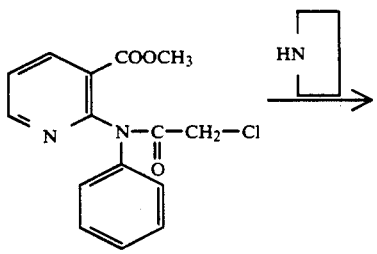
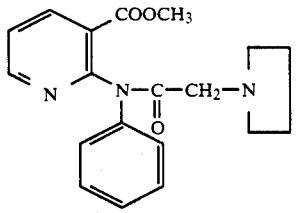

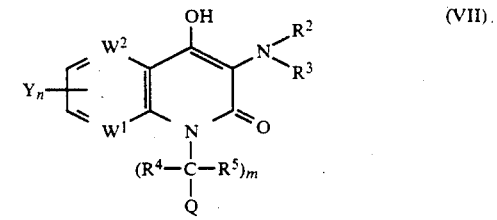

To a gently refluxing stirred solution of 1 gram (g) (3.3 (mM) of 3-pyridinecarboxylic acid- 2((chloroacetyl)phenylamino)methyl ester in t-butylmethyl ether, 1.1 milliter (mL) pyrrolidine (13.2 mM) is added. The reaction mixture is refluxed for 2.5 hours, diluted with t-butylmethyl ether, and washed with water. The water layer is extracted with t-butylmethyl ether, and the combined organic phases are washed with a saturated aqueous sodium chloride (NaCl) solution, dried over anhydrous sodium sulfate (Na2SO4) and then concentrated in vacuo to give 1.1 g (93% yield) of title compound, a tan solid.

IR (CHCl1) 1685, 1725 cm$^{-1}$,
NMR (CDCl2) δ3.25 (N—CO—CH2—N).

While the present invention has been described in conjunction with the specific embodiments set forth above, many alternatives, modifications, and variations thereof will be appoint to those of ordinary skill in the art. All such alternatives, modifications and variations are intended to fall within the spirit and scope of the present invention.

What is claimed is:

1. A process for preparing a compound of the Formula $$\text{(VII)}$$

wherein
$W^1$ and $W^2$ independently represent —CH= or —N=;
$R^2$, $R^3$, $R^4$ and $R^5$ independently represent H, alkyl having from 1 to 12 carbon atoms, alkenyl having from 3 to 8 carbon atoms, alkynyl having from 3 to 8 carbon atoms, alkoxyalkyl having from 1 to 6 carbon atoms in the alkoxy portion and from 2 to 6 atoms in the alkyl portion thereof, hydroxyalkyl having from 2 to 8 carbon atoms, cycloalkyl having from 3 to 8 carbon atoms, acyloxyalkyl having from 1 to 6 carbon atoms in the acyloxy portion and from 2 to 8 carbon atoms in the alkyl portion thereof, and —$R^6$—$CO_2R^0$ wherein $R^6$ represents an alkylene group having from 1 to 6 carbon atoms and $R^0$ represents hydrogen or an alkyl group having from 1 to 6 carbon atoms, with the provisos that the OH of the hydroxyalkyl group and the acyloxy of the acyloxyalkyl group are not joined to the same carbon atom as another heteroatom and that, when $R^2$ and/or $R^3$ are alkenyl or alkynyl, there is at least one carbon-carbon single bond between the nitrogen atom and the carbon-carbon double or triple bond and also with the proviso that R³ does not independently represent hydrogen;

in addition, one of R² or R³ can be an aryl group or an aromatic heterocyclic group, either of which can be substituted with one to three substituents Y as defined below;

in further addition, R² and R³ can be joined together to represent a ring which can contain from 2 to 8 carbon atoms, said ring optionally containing a —O—, —S— and/or —NR⁴— heteroatomic group (wherein R⁴ is as defined above) and/or optionally containing a carbon-carbon double bond, and said ring optionally being substituted with one to three additional substituents R⁷ which substituents may be the same or different and are each independently selected from OH with the proviso that OH is not on a carbon already joined to a hetero atom, —O—acyl having from 1 to 6 carbon atoms, hydroxyalkyl having from 1 to 8 carbon atoms, alkoxyalkyl having from 1 to 6 carbon atoms is each alkyl portion thereof, alkyl having from 1 to 6 carbon atoms, alkenyl having from 3 to 8 carbon atoms, alkynyl having from 3 to 8 carbon atoms, —COOR¹⁰ wherein R¹⁰ is H, alkyl or aryl, or any two R⁷ substituent groups may represent a hydrocarbon ring having from 4 to 8 total carbon atoms;

in still further addition, both R² and R³ can be joined together to represent a polycyclic ring, which polycyclic ring can optionally be substituted by one to three substituents groups R⁷ is defined above;

m is an integer of from 0 to 3;

n is an integer of from 0 to 2;

Q represents an aryl or an aromatic heterocyclic group which can optionally be substituted with 1 to 3 substituents Y as defined below;

each Y substituent is independently selected from the group consisting of hydroxy, alkyl having from 1 to 6 carbon atoms, halogen, NO₂, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, hydroxyalkyl having from 1 to 6 carbon atoms, —S-(O)$_n$—R⁸ (wherein R⁸ represents alkyl having from 1 to 6 carbon atoms and n is as defined above), —SO₂NH₂, —CO—R⁹ (wherein R⁹ represents OH, —NH—R⁸ or —O—R⁸, where R⁸ is as defined above), —O—B—COR⁹ (wherein B represents an alkylene group having from 1 to 4 carbon atoms and R⁹ is as defined above), —NH₂, —NHCHO, —NH—CO—R⁹ (wherein R⁹ is as defined above, with the proviso that it is not hydroxy), —NH—COCF₃, —NH—SO₂R⁸ (wherein R⁸ is as defined above), and —NHSO₂CF₃, comprising contacting an amino acetamide compound of the formula:

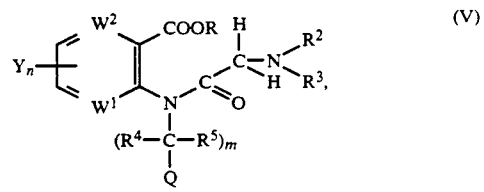

wherein

Y, W¹, W², R², R³, R⁴, R⁵, Q, m and n are as defined hereinbefore, and

R is any of the values for R⁴ or R⁵ with the proviso that R is not hydrogen, with a base effective to selectively remove a proton from the methyl group of said amino acetamide compound (V) in order to intramolecularly cyclize said compound to the bicyclic compound of formula (VII).

2. The process of claim 1, wherein as to the amino acetamide compound of formula (V), Y is hydrogen, W¹ is nitrogen, W² is CH, R is methyl, m is zero, R² and R³ are joined together to represent a ring of four carbon atoms and Q is phenyl.

3. The process of claim 1, wherein as to the bicyclic compound of formula VII, Y is hydrogen, W¹ is nitrogen, W² is CH, m is zero, Q is phenyl and R² and R³ are joined together to represent a ring of four carbon atoms.

4. The process of claim 1, wherein in the base is potassium t-butoxide.

5. The process of claim 1, wherein the contacting is performed in the presence of the solvent dimethylformamide.

* * * * *